United States Patent

Patrini et al.

[11] Patent Number: 5,510,541
[45] Date of Patent: Apr. 23, 1996

[54] PROCESS FOR THE TELOMERIZATION OF CONJUGATED DIENES AND SUITABLE CATALYST THEREFOR

[75] Inventors: Renata Patrini; Mario Marchionna, both of Milan, Italy

[73] Assignee: Snamprogetti S.p.A., Milan, Italy

[21] Appl. No.: 201,991

[22] Filed: Feb. 25, 1994

[30] Foreign Application Priority Data

Mar. 3, 1993 [IT] Italy .................. MI93A0403

[51] Int. Cl.$^6$ .................................. C07C 41/10
[52] U.S. Cl. .................. 568/654; 568/658; 568/673; 568/690
[58] Field of Search ............... 568/673, 690, 568/654, 658

[56] References Cited

U.S. PATENT DOCUMENTS 4,142,060 2/1979 Kuntz ........................ 568/840

FOREIGN PATENT DOCUMENTS 0296550 12/1988 European Pat. Off. .
0436226 7/1991 European Pat. Off. .
2733516 2/1978 Germany .

OTHER PUBLICATIONS

Chemical Abstracts, vol. 113, No. 151758, 1990 (J. Mol. Catal., vol. 59, No. 1, 1990, pp. 1–9).

*Primary Examiner*—Robert Gerstl
*Attorney, Agent, or Firm*—Oblon, Spivak, McClelland, Maier & Neustadt

[57] ABSTRACT

Mono-alkadienyl alkyl ethers and di-alkadienyl alkyl ethers are prepared by telomerization of a conjugated diene, by causing said conjugated diene to react with an aliphatic alcohol or an aliphatic diol respectively, by operating in an aqueous/organic biphasic liquid system, in the presence of a catalytic system formed by:

(a) a palladium salt or complex;

(b) an alkyl-, alkylcycloalkyl-, or alkylarylphosphine ligand, bearing an acidic or neutral hydrophylic moiety, having the formula:

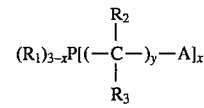

wherein $R_1$, $R_2$, $R_3$, x and y are as defined in the disclosure; and (c) an either inorganic or organic base.

17 Claims, No Drawings

PROCESS FOR THE TELOMERIZATION OF CONJUGATED DIENES AND SUITABLE CATALYST THEREFOR

The present invention relates to a process for preparing mono- and di-alkadienyl alkyl ethers by means of the telomerization of conjugated dienes and to a catalytic system suitable for that purpose, Alkadienyl alkyl ethers are well known compounds in the art, which find use in particular as solvents for paints, components in cosmetic formulations and crosslinking agents for organic polymers. The reaction of telomerization of conjugated dienes (for example, butadiene, isoprene, and so forth), with a compound bearing an active hydrogen atom (for example water, alcohol, carboxy acids, amines, ammonia, and so forth) is known to be catalyzed by transition metal compounds (in particular palladium compounds) and phosphines (J. Tsuji, Adv. Organomet. Chem. 17, 141–193, 1979; R. F. Heck, "Palladium reagents in organic syntheses" 1990 Academic Press).

A problem met these with telomerization reactions derives from the difficulty of separating and recovering the catalyst from the reaction products.

On considering the high cost of the catalyst, it is evident that simplifying the recycle of said catalyst would lead to a more advantageous process from the financial view point. In this regard, one should observe that the catalyst is soluble in the reaction system and that, owing to the thermal instability thereof, not always the separation of the reaction products by distillation without decomposing the catalyst is possible. Therefore, the use of sulfonated aryl phosphines in the telomerization reactions was proposed in the art, as disclosed in the following patents: FR 2,366,237, DE 2,733, 516, EP 296,550 and EP 436,226, which make it possible the catalyst to be separated from the reaction products by means of a simple phase separation. In fact, said phosphines endow the catalyst with a hydrophilic character, which catalyst is consequently selectively kept in the polar phase, whilst the reaction products remain in the a polar phase.

The present Applicant found now, according to the present invention, that the use of particular alkyl, alkylcycloalkyl or alkylaryl phosphines bearing an acidic or neutral hydrophilic moiety in their molecule, as ligands for palladium, in a process of telomerization of conjugated dienes, makes it possible the catalyst activity and selectivity to the desired telomers to be unexpectedly improved, because the telomerization exclusively or substantially exclusively takes place at the conjugated function.

The present Applicant found furthermore that the use of such ligands in an organic/aqueous two-phase liquid reaction vehicle, makes it possibile the catalyst and the reaction products to be easily separated at the end of the telomerization reaction.

In accordance therewith, the present invention relates to a process for preparing mono-alkadienyl alkyl ethers (IV) by means of the catalyzed reaction of a conjugated diene (I) with an aliphatic alcohol (II):

$$2\,CH_2=\underset{R^i}{C}-CH=\underset{R^{ii}}{CH} + R^{iii}-OH \longrightarrow$$

(I)　　　　(II)

-continued
$$CH_2=\underset{R^i}{C}-CH_2-\underset{R^{ii}}{CH}-CH_2-\underset{R^i}{C}=CH-\underset{R^{iii}}{CH}-OR^{iii}$$

(IV)

and for preparing di-alkadienyl alkyl ethers (V) by means of the catalyzed reaction of said conjugated diene (I) with an aliphatic diol (III):

$$4\,CH_2=\underset{R^i}{C}-CH=\underset{R^{ii}}{CH} + HO-R^{iv}-OH \longrightarrow$$

(I)　　　　　　(III)

$$[CH_2=\underset{R^i}{C}-CH_2-\underset{R^{ii}}{CH}-CH_2-\underset{R^i}{C}=CH-\underset{R^{ii}}{CH}-O]_2R^{iv}$$

(V)

wherein:
- $R^i$ represents a hydrogen atom or methyl radical,
- $R^{ii}$ represents a hydrogen atom, a $C_1$–$C_8$ alkyl radical, or a phenyl radical,
- $R^{iii}$ represents a $C_1$–$C_8$ alkyl radical, and
- $R^{iv}$ represents a $C_2$–$C_8$ alkylene radical;

characterized in that the reaction between the conjugated diene (I) and the alcohol (II) or diol (III) is carried out in an aqueous/organic two-phase liquid system, in the presence of a catalytic system formed by:

(a) a palladium salt or complex;
(b) an alkyl-, alkylcycloalkyl-, or alkylarylphosphine ligend, bearing an acidic or neutral hydrophylic moiety, having the formula (VI):

$$(R_1)_{3-x}P[(-\underset{R_3}{\overset{R_2}{C}}-)_y-A]_x \qquad (VI)$$

wherein:

A represents a hydrophilic moiety of sulfate ($-SO_3M$), phosphate ($-PO_3M_2$), hydroxy ($-OH$) or alkoxy ($-OR_4$) character (in which M represents H, Li, Na, K and $NH_4$ and $R_4$ represents a $C_1$–$C_5$ alkyl moiety), $R_1$ represents the hydrogen atom, a $C_1$–$C_5$ alkyl moiety, a $C_5$–$C_6$ cycloalkyl moiety, a $C_1$–$C_5$ alkoxy moiety, an aryl (in particular, phenyl) radical or an aryloxy moiety, with said aryl moieties being optionally substituted with one or more halogen atoms or $C_1$–$C_5$ alkyl moieties;

$R_2$ and $R_3$ represent, each indipendently, a hydrogen atom or a methyl radical, x is a numeral comprised within the range of from 1 to 3, y ia a numeral comprised within the range of from 1 to 6; and (c) an either inorganic or organic base.

The conjugated dienes (II) which are submitted to the process according to the present invention are advantageously selected from 1,3-butadiene, isoprene, piperylene, methylpentadiiene and phenylbutadiene. Preferably used is 1,3-butadiene. The conjugated dienes may be used either in pure, or substantially pure form, or as hydrocarbon streams containing one or more conjugated dienes, for example, a $C_4$ fraction containing butadiene, or a $C_5$ fraction containing isoprene and piperylene.

The aliphatic alcohol (II) which is submitted to the process according to the present invention is preferably selected from methanol and ethanol.

The aliphatic diol (II) which is submitted to the process according to the present invention is preferably selected from ethylene glycol and propylene glycol.

The palladium salt or complex (a) of the catalytic system, used in the process according to the present invention, may be selected from palladium acetyl acetonate, π-allylpalladium chloride, palladium chloride, palladium nitrate, palladium acetate, π-allylpalladium acetate, palladium bis(benzylidene acetyl acetonate), palladium bis(cyclooctadiene) and bis (π-allyl)palladium. The active palladium species in the telomerization reaction is thought to be zerovalent or univalent palladium. However, both palladium-(O) and palladium (II) compounds can be used, because the latter are easily reduced by the same conjugated diene, or by basic compounds present in the reaction environment. A particularly preferred palladium compound is bis(benzylidene acetyl acetonate).

The preferred phosphinic ligands (b) for the catalytic system are those which are represented by formula (VI) in which $R_1$ is selected from ethyl, cyclohexyl and phenyl radicals; $R_2$ and $R_3$ represent a hydrogen atom; A represents the sulfate moiety —$SO_3M$, with M standing for a sodium atom; and x is either 1 or 2.

In particular, the use of sulfonated phosphines bearing their sulfonic group on their alkylic portion makes it possible the selectivity and stability of the catalytic system to be enhanced.

Specific examples of such phosphines (b) are:

$Et_2PCH_2CH_2SO_3Na$ (Et=Ethyl);

$cyP(CH_2CH_2SO_3Na)_2$, (cy=cyclohexyl); and $PhP(CH_2CH_2SO_3Na)_2$ (Ph=phenyl).

The synthesis of the above specified phosphines, or of similar phosphines, is per se known and is reported, e.g., in U.S. Pat. No. 4,689,437, EP 350,921 and in S. Ganguly, J. T. Mague, D. M. Roundhill, Inorg. Chem., 31, 3500 (1992).

The inorganic base used as the component (c) of the catalytic system can be selected from oxides, hydroxides, carbonates and alkoxides of alkali or alkaline-earth metals, or from organic bases, and preferably is sodium hydroxide.

In the process according to the present invention, said component (a) of the catalytic system is present in the reaction vehicle at a level of from 0.000001 to 1 molar, and preferably of from 0.00001 to 0.1 molar; said component (b) is present at a level of from 0.00001 to 10 molar, and preferably of from 0.0001 to 0.1 molar, and said component (c) is present at a Level of from 0.00001 to 10 molar, and preferably of from 0.0001 to 0.1 molar.

Furthermore, the process is carried out with a molar ratio of conjugated diene:Pd comprised within the range of from 10 to 100,000, and preferably of from 100 to 10,000, and with a molar ratio of aliphatic alcohol (II):conjugated diene comprised within the range of from 0.1 to 100, and preferably of from 1 to 50.

In the process according to the present invention, the reaction system is an aqueous/organic two-phase liquid system. The organic phase can be constituted by a liquid hydrocarbon such as a paraffin, an olefin, a non-conjugated diene or an aromatic hydrocarbon, or by the same conjugated diene, used in an excess amount.

The added water amount, which is used in order to favour the phase separation, should be large enough in order to secure the phase separation, but in the meanwhile it should not favour the competition of the alcohol in the nucleophilic attack of water in the telomerization reaction.

In particular, it was found that good results are obtained when the process is carried out by operating with a weight ratio of aliphatic alcohol (II) or aliphatic diol (III) to $H_2O$ comprised within the range of from 100 to 0.001, and preferably of from 20 to 0.1.

In particular, when as the reactant a water soluble aliphatic alcohol (II) or aliphatic diol (III) is used, the process is carried out with an aqueous-alcoholic phase of such an alcohol or diol. In this case, at reaction end, the organic phase containing the mono- or di-alkadienylalkyl ether is separated by an aqueous-alcoholic phase containing the catalytic system. Therefore, the mono- or di-alkadienil alkyl ether can be separated from the organic phase, and the catalyst can be separated from said aqueous-alcoholic phase. However, said aqueous-alcoholic phase containing the catalyst is preferably recycled without any preliminary-separation.

When the aliphatic alcohol (II) or diol (III) is insoluble or sparingly soluble in water, at the end of the telomerization reaction aqueous catalyst phase and an organic phase will be obtained, with the latter, besides the mono- or di-alkadienyl alkyl ether, containing any unreacted alcohol (II) or diol (III). In that case, said alcohol or diol must be separated.

In the process according to the present invention, the reaction is furthermore carried out at a temperature comprised within the range of from 20° to 120° C. and under a pressure comprised within the range of from 0.1 to 10 MPa and preferably under a pressure equal to the vapour pressure of the components of the reaction mixture. By operating under the above conditions, conversions of conjugated diene can be obtained which may reach values of 99% or even more, with initial reaction rates of approximately 10 $s^{-1}$ (converted mols of conjugated diene per palladium mol per second) and very high selectivity values to alkadienyl-alkyl ethers (comprised within the range of from 80 to 100%). The resulting byproducts generally are either dimers of the conjugated diene, of higher telomers.

The following experimental examples are reported in order to better illustrate the present invention.

EXAMPLE 1

This example illustrates the use of the catalytic system according to the present invention in the reaction of telomerization of 1,3-butadiene with methanol at 80° C. in a batch reactor.

Inside an autoclave equipped with magnetic-driven stirring means, of 100 ml of volume, 0.095 mmol of $Pd(dba)_2$, (dba=dibenzylidene acetone), 0.57 mmol of $Et_2PCH_2CH_2SO_3Na$, 0.76 mmol of NaOH, 185 mmol of 1,3-butadiene, 285 mmol of methanol (about 11.5 ml), 1 ml of water and 24 ml of hexane are mixed with one another. The operation is carried out under a blanketing nitrogen atmosphere.

The reaction mixture is heated up to the temperature of 80° C. By operating in that way, after a three-hour reaction, a conversion of 1,3-butadiene of 98% was obtained, with a selectivity to alkadienylmethyl ethers of 95% and consequently a yield of the latter of 93%.

EXAMPLE 2

This example displays that the conversion and selectivity values remain good even when the catalytic system is recycled.

The catalytic system from Example 1 dissolved in the MeOH-H$_2$O phase after separating the hydrocarbon phase is used. After make-up of reacted methanol, 24 ml of hexane and 139 mmol of butadiene are added; the reaction is carried out under the same conditions as of Example 1.

After a 3-hour reaction, a conversion of 1,3-butadiene of 90% was obtained with a selectivity to telomers of 96%, with the yield of the latter being hence of 86%.

EXAMPLE 3

This example demonstrates that a high performance of the catalytic system also obtained with other sulfonated phosphines.

The process is carried out under the same conditions as of Example 1, with the catalytic system being however constituted by 0.095 mmol of Pd(dba)$_2$, 0.12 mmol of cyP(CH$_2$CH$_2$SO$_3$Na)$_2$, (cy=cyclohexyl), 0.76 mmol of NaOH, 185 mmol of 1,3-butadiene, 285 mmol of methanol, 1 ml of water and 24 ml of hexane. The operation is carried out under a blanketing nitrogen atmosphere.

The reaction mixture is heated at a temperature of 80° C. By operating in that way, after a three-hour reaction a conversion of 1,3-butadiene of 69% was obtained with a selectivity to alkadienyl-methyl ethers of 94%, with the yield of the latter being therefore of 65%.

Also in this case, the products are easily separated from the catalyst.

EXAMPLE 4 (COMPARISON EXAMPLE)

This example shows that the absence of the base causes a decrease in catalytic system performance.

The process is carried out under the same conditions as of Example 1, but without the base.

After a three-hour reaction, a conversion of 72% is obtained with a selectivity to telomers of 96%, with the telomer yield being of 69%.

EXAMPLE 5 (COMPARISON EXAMPLE)

This example shows that according to the present invention, the yields to desired products are maximized, with the other experimental conditions being the same, as compared to the prior art.

The process is carried out in the same way and according to the same experimental modalities as disclosed in Example 1.

The catalytic system is prepared as disclosed in DE 2,733,516 and is constituted by 55 mg of Pd(dba)$_2$, 0.38 mmol of PhP(PhSO$_3$Na)$_2$, 172 mmol of 1,3-butadiene, 285 mmol of methanol (about 11.5 ml), 1 ml of water and 24 ml of hexane. The whole operation is carried out under a blanketing nitrogen atmosphere.

The reaction mixture is heated up to the temperature of 80° C. By operating in that way, after a three-hour reaction a conversion of 1,3-butadiene of 66% was obtained with a selectivity to alkadienyl-methyl ethers of 92%, corresponding to a yield of the latter of 61%.

Furthermore, at the end of the reaction, the presence may be observed of metal palladium and when the aqueous phase is recycled (as in Example 2), a further reaction does not occur.

EXAMPLE 7

In this example, ethanol is used as the aliphatic alcohol.

The process is carried out under the sane operating conditions as of Example 1, with the same catalytic systems and with 104 mmol of 1,3-butadiene, 285 mmol of ethanol (about 16.6 ml), 1 ml of water and 24 ml of hexane: the operation is carried out under e blanketing nitrogen atmosphere.

The reaction mixture is heated up to the temperature of 80° C. By operating in that way, after a three-hour reaction a conversion of 1,3-butadiene of 97% was obtained with a selectivity to alkadienyl-ethyl ethers of 84%, and a yield of the latter of 82%.

We claim:

1. Process for preparing mono-alkadienyl alkyl ethers (IV) by means of the catalyzed reaction of a conjugated diene (I) with an aliphatic alcohol (II):

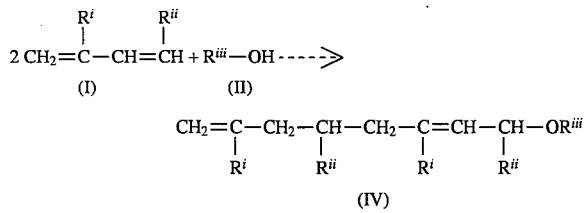

and for preparing di-alkadienyl alkyl ethers (V) by means of the catalyzed reaction of said conjugated diene (I) with an aliphatic diol (III):

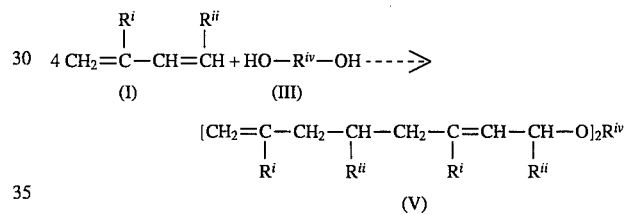

wherein:

$R^i$ represents a hydrogen atom or a methyl radical, $R^{ii}$ represents a hydrogen atom, a $C_1$–$C_8$ alkyl radical, or a phenyl radical, $R^{iii}$ represents a $C_1$–$C_8$ alkyl radical, and $R^{iv}$ represents a $C_2$–$C_8$ alkylene radical;

characterized in that the reaction between the conjugated diene (I) and the alcohol (II) or diol (III) is carried out in an aqueous/organic two-phase liquid system, wherein the organic phase comprises a liquid hydrocarbon, in the presence of a catalytic system formed by:

(a) a palladium salt or complex;

(b) an alkyl-, alkylcycloalkyl-, or alkylaryl-phosphine ligand, bearing an acidic or neutral hydrophylic moiety, having the formula (VI):

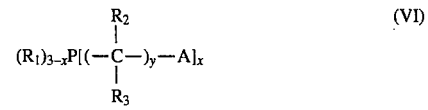

wherein:

A represents a hydrophylic moiety of sulfate (—SO$_3$M), phosphate (—PO$_3$M$_2$), hydroxy (—OH) or alkoxy (—OR$_4$) character (in which M represents H, Li, Na, K and NH$_4$ and R$_4$ represents a $C_1$–$C_5$ alkyl moiety), R$_1$ represents a hydrogen atom, a $C_1$–$C_5$ alkyl moiety, a $C_5$–$C_6$ cycloalkyl moiety, a $C_1$–$C_5$ alkoxy moiety, an aryl radical or an aryloxy moiety, with said aryl moieties being optionally substituted with one or more halogen atoms or $C_1$–$C_5$ alkyl moieties;

$R_2$ and $R_3$ represent, each independently, a hydrogen atom or a methyl radical, x is a numeral comprised within the range of from 1 to 3, y is a numeral comprised within the range of from 1 to 6; and (c) an inorganic or organic base.

2. Process according to claim 1, characterized in that said conjugated diene (I) is selected from 1,3-butadiene, isoprene, piperylene, methyl pentadiene and phenyl butadiene.

3. Process according to claim 2, characterized in that said conjugated diene (I) is 1,3-butadiene.

4. Process according to claim 1, characterized in that said aliphatic alcohol (II) is selected from methanol and ethanol.

5. Process according to claim 1, characterized in that said aliphatic diol (III) is selected from ethylene glycol and propylene glycol.

6. Process according to claim 1, characterized in that said palladium salt or complex (a) is selected from palladium acetyl acetonate, π-allyl palladium chloride, palladium chloride, palladium nitrate, palladium acetate, π-allyl palladium acetate, palladium bis(benzylidene acetyl acetonate), palladium bis(cyclooctadiene) and bis (π-allyl) palladium.

7. Process according to claim 6, characterized in that said palladium compound is palladium bis(benzylidene acetyl acetonate).

8. Process according to claim 1, characterized in that said alkyl-, alkylcycloalkyl-, or alkylaryl phosphine ligand (b) is represented by formula (VI) in which $R_1$ is selected from ethyl, cyclohexyl and phenyl radicals; $R_2$ and $R_3$ represent a hydrogen atom; A represents the sulfate moiety $-SO_3M$, with M representing a sodium atom; and x is either 1 or 2.

9. Process according to claim 8, characterized in that said ligand is selected from:

$Et_2PCH_2CH_2SO_3Na$ (Et=Ethyl);

$cyP(CH_2CH_2SO_3Na)_2$, (cy=cyclohexyl); and $PhP(CH_2CH_2SO_3Na)_2$ (Ph=phenyl).

10. Process according to claim 1, characterized in that said inorganic base (c) is selected from oxides, hydroxides, carbonates and alkoxides of alkali or alkaline-earth metals.

11. Process according to claim 1, characterized in that said component (a) of the catalytic system is present in the reaction vehicle at a level of from 0.000001 to 1 molar; said component (b) is present at a level of from 0.00001 to 10 molar, and said component (c) is present at a level of from 0.00001 to 10 molar.

12. Process according to claim 1, characterized in that the process is carried out with a molar ratio of conjugated diene: Pd comprised within the range of from 10 to 10,000, and with a molar ratio of aliphatic alcohol (II) or aliphatic diol (III): conjugated diene comprised within the range of from 0.1 to 100.

13. Process according to claim 1, characterized in that the two-phase liquid reaction vehicle comprises an organic phase of a liquid hydrocarbon, and an aqueous phase containing methyl or ethyl alcohol.

14. Process according to claim 13, characterized in that said liquid hydrocarbon is a paraffin, an olefin, a non-conjugated diene or an aromatic hydrocarbon, or by the same conjugated diene, used in an excess amount.

15. Process according to claim 13, characterized in that, in said aqueous phase, the weight ratio of methyl or ethyl alcohol to $H_2O$ is comprised within the range of from 100 to 0.001.

16. Process according to claim 1, characterized in that the reaction is carried out at a temperature comprised within the range of from 20° to 120° C. and under a pressure of from 0.1 to 10 MPa.

17. Process according to claim 1, characterized in that it furthermore comprises separating, at reaction end, an organic phase containing the monoalkadienyl alkyl ether or the di-alkadienyl alkyl ether from an aqueous-alcoholic phase containing the catalytic system, and in that said mono- or di-alkadienyl alkyl ether is recovered from the organic phase and the catalyst is recovered from said aqueous-alcoholic phase.

* * * * *